United States Patent [19]

Ash et al.

[11] Patent Number: 4,498,902
[45] Date of Patent: Feb. 12, 1985

[54] CATHETER GUIDE

[75] Inventors: Stephen R. Ash, Lafayette; Gordon C. Wolf, Rossville; Richard Bloch, Lafayette, all of Ind.

[73] Assignee: Purdue Research Foundation, West Lafayette, Ind.

[21] Appl. No.: 469,096

[22] Filed: Feb. 23, 1983

Related U.S. Application Data

[63] Continuation of Ser. No. 321,128, Nov. 13, 1982, abandoned, which is a continuation of Ser. No. 92,031, Nov. 7, 1979, abandoned.

[51] Int. Cl.³ .................. A61B 17/34; A61M 25/00
[52] U.S. Cl. .................................. 604/164; 604/281; 128/772
[58] Field of Search ............... 604/158, 160, 164, 166, 604/171, 281, 163; 128/341, 772

[56] References Cited

U.S. PATENT DOCUMENTS 3,559,643  2/1971  Pannier et al. ...................... 604/171
3,742,958  7/1973  Rundles ............................... 604/164
3,769,975  11/1973  Nimoy et al. ....................... 604/165

Primary Examiner—Stephen C. Pellegrino
Attorney, Agent, or Firm—O'Rourke & Harris

[57] ABSTRACT

A slotted catheter emplacement guide of one piece construction which simplifies emplacement of a peritoneal catheter and also permits insertion through a very small abdominal opening.

4 Claims, 6 Drawing Figures

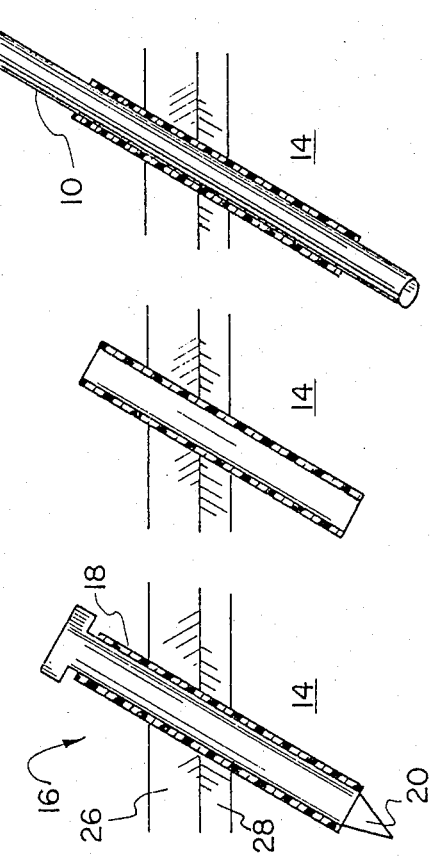

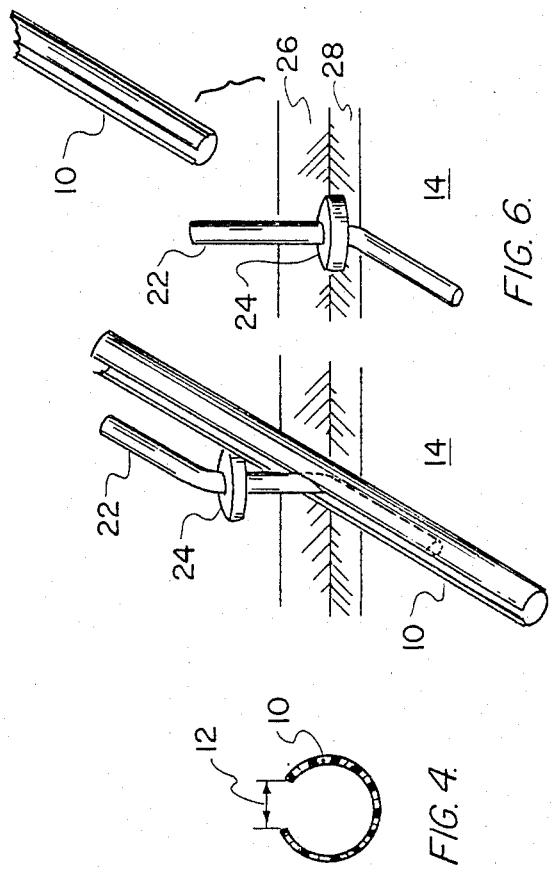

CATHETER GUIDE

RELATED INVENTION

This application is a continuation of our co-pending U.S. patent application Ser. No. 321,128 filed Nov. 13, 1982 now abandoned, which application was a continuation of our co-pending U.S. patent application Ser. No. 092,031 filed Nov. 7, 1979 and now abandoned.

FIELD OF THE INVENTION

This invention relates to catheter emplacement devices and more particularly to a semi-rigid, slotted guide which simplifies present catheter emplacement and guide withdrawal techniques.

BACKGROUND OF THE INVENTION

Peritoneal dialysis is a procedure in which a sterile, balanced salt solution is placed into the peritoneal cavity. The solution plus impurities removed from the blood is then removed at some time later (one-half to 10 hours) and replaced. During this exchange of fluid, toxic soluble materials are removed from the patient. Peritoneal dialysis is effective for treatment of kidney failure and has been utilized for about thirty years for this purpose. For the successful use of peritoneal dialysis, however, an access device must be utilized which allows continuous access to the peritoneum, without repeated puncture, and without subsequent infection along the prosthesis. A variety of prostheses have been used in the past, but by far the most successful has been the Tenckhoff catheter. Developed in the mid 1960's, this catheter is a silicone rubber tube with numerous drainage holes on its inner portion. One or two dacron "cuffs" are placed in the subcutaneous tissue or in the muscle layer of the patient. These cuffs serve to limit peritoneal fluid leakage out of the peritoneum and bacterial migration along the catheter from the outside. These cuffs are approximately ½" in total diameter and the silicone tube is slightly less than ¼" in diameter.

The Tenckhoff catheter may be placed surgically, making an incision over the abdominal musculature which is large enough to allow placement of the cuffs in the subcutaneous tissue. Alternately, the Tenckhoff catheter may be placed using a "Trocar[ developed by Dr. Tenckhoff, and described in an article by him, "Catheter Implantation", *Dialysis Transplantation*, October 1972, p. 18-20. This Trocar allows placement of the smaller silicone tube portion of the catheter inside the abdominal cavity, and placement of the larger cuff outside the abdominal cavity in the subcutaneous tissue, all utilizing the single insertion device. This device conforms to the shape of the silicone tube, and has a wide channel for the cuff. The device separates, after the insertion of the silicone tube portion into the abdomen, thus reducing the difficulty of having the cuff portion go through the narrowest part of the trocar device.

Although this trocar may be successfully used at the bedside by any physician, it does have several drawbacks. First, the steel portion entering the abdomen is relatively large, being approximately ¼" in diameter. Second, the insertion of the abdominal portion must be done "blind" occasionally causing difficulty in cases of previous surgical operations. Third, the device is somewhat bulky to operate and separation of halves and removal of the halves around the cuff is often difficult. Fourth, the device is not airtight, therefore, use during inspection of the abdomen under peritoneoscopy is difficult (since a pressurized volume of air cannot be kept in the abdonmen with this device inserted).

Since the development of the Tenckhoff trocar, there have been no alternate or new devices for placement of the Tenckhoff catheter. Other implantable access devices have been developed utilizing the dacron cuff for tissue ingrowth. These have been used for arteriovenous access (for hemodialysis) and for long term venous access (as for hyperalimentation).

SUMMARY OF THE INVENTION

The object of this invention is to provide a device which easily and safely permits placement of cuffed access devices into the body, with proper placement of the dacron cuff and minimal penetration hole size into the body cavity.

The catheter introducer guide has several advantages over the standard Tenckhoff introducer and versus surgical placement. Another object is to provide a device such that the hole made into the peritoneum (or other cavity) may be smaller than that made by a scalpel or by the Tenckhoff introducer as the catheter guide of this invention may expand in diameter after placement. Another object of this invention is to provide a catheter guide which will direct the entire length of the silicone rubber catheter into the abdomen rather than just the portion which goes through the abdominal wall.

Yet another object of this invention is to provide a guide which is easy to use and less bulky than the Tenckhoff introducer which has four parts.

Still another object of this invention is to provide a device which may be utilized with a standard trocar sheath and which can still be made to be air tight. This type of trocar sheath should also be compatible with visual inspection of the peritoneum under air of CO2 distention (peritoneoscopy).

BRIEF DESCRIPTION OF THE DRAWINGS

The accompanying drawings illustrate a complete embodiment of the invention according to the best mode so far devised for the practical application of the principles thereof, and in which:

FIG. 1 is a schematic view of a trocar device inserted into the peritoneum.

FIG. 2 is a schematic view of the trocar of FIG. 1 after removal of the obturator so that only the sheath remains.

FIG. 3 is a schematic view showing insertion of the guide of this invention.

FIG. 4 is an end cross sectional view of the guide taken along line A—A in FIG. 3.

FIG. 5 is a schematic view of the initial insertion of the flexible catheter through the guide shown in FIG. 3.

FIG. 6 is a schematic view of the final implanted position of the catheter shown in FIG. 5, with the guide in retracted position.

DESCRIPTION OF THE PREFERRED EMBODIMENT OF THE INVENTION

The invention consists of a long, approximately 12 inches by ¼ inches, guide 10 of suitable semi-rigid plastic. The guide 10 is generally "cylindrical" but with a slot 12 in its entire length. The guide is "rolled" into a diameter slightly smaller than its normal diameter prior to insertion which causes slight outwardly expansionist bias in said guide. The abdomen is entered through the subcutaneous tissue 26, and the anterior abdominal musculature 28 by means of a trocar 16 consisting of a sheath 18 and a pointed filling piece 20 called an obturator. The obturator 20 is then removed, and at this point the abdomen may be inflated with air and/or other gas, and an optical inspection device may be placed through the trocar sheath. The optical instrument (not shown) may then be removed (optical inspection is not a necessary part of the procedure). The plastic rolled guide 10 may then be introduced into the abdomen 14 through the trocar sleeve 18. The guide 10 may then be introduced through a trocar of relatively small diameter because of its unique slotted construction which both facilitates catheter insertion and permits a preinsertion bias to be exerted upon the guide.

After the catheter guide 10 has been placed, the silicone rubber portion 22 of the Tenckhoff catheter may be introduced into the inside of the catheter guide. The silicone rubber is brought out through the slot in the catheter guide, (as shown in FIG. 5) just in front of the dacron cuff 24. The silicone rubber portion of the catheter is then advanced into the abdomen. The cuff 24 comes to lie at the anterior abdominal musculature 28 which is the proper place for fibrous ingrowth, as shown in FIG. 6, and then the catheter guide 10 may be removed with the slot 12 opening to pass the silicone rubber catheter. The rest of the portion of the Tenckhoff catheter 22 is tunneled subcutaneously to a second opening, as described by Tenckhoff.

It will be obvious to those skilled in the art that the catheter introducer guide herein, while described in conjunction with peritoneal dialysis technique, may also be used in other surgical environments where a flexible catheter is used.

What is claimed:

1. A catheter placement unit having a trocar with a substantially cylidrical sheath, the improvement comprising:

guide means having an exterior surface and an interior surface which define a guide wall therebetween with said guide wall having a normally curved cross-sectional area of preselected diameter; and said guide means having an opening of adjustable dimensions extendable throughout the entire length thereof, said guide means being semi-rigid such that, when compressive forces are applied to the said exterior surface of said guide means the guide wall is coiled so that the diameter of said guide wall is reduced, but when said compressive forces are removed, said guide wall tends to return to its said normal diameter, with said guide means being readily deformable to allow adjustment of said diameter of said guide means with said guide means being rolled into an adjusted diameter to facilitate utilization placement and movement of said guide means relative to said sheath of said trocar, and said opening of adjustable dimensions allowing said guide means to receive a catheter of a material suitable for causing said deformation of said guide means so that said catheter may be inserted through said opening exterior of a patient, and so that said guide means may be withdrawn from a patient without disturbing the positioning and integrity of said catheter.

2. A catheter placement unit having a trocar with a substantially cylindrical sheath, the improvement comprising:

a guide having a generally tubular configuration about its longitudinal axis;

said guide being made of a single curved piece of semirigid material having opposite longitudinally extending sides which are adjacent to one another and outer and inner surfaces which define a generally tubular wall therebetween having a preselected effective diameter;

said opposite longitudinally extending sides providing a slot extendable along the entire longitudinal length of said guide whereby the exertion of compressive forces on the outer surfaces of the guide causes rolling of the generally tubular wall to reduce the effective diameter of the guide, said semirigid material being biased toward enlargement of the diameter of said guide when the effective diameter of said guide is reduced by said exertion of compressive forces which causes the generally tubular wall to be coiled, and whereby the exertion of expansion forces on the inner surface of the guide causes unrolling of the generally tubular wall to enlarge the effective diameter of the guide, so that the effective diameter of said guide is such that frictional engagement of said guide with said sheath of said trocar exists when said guide and sheath are coaxially positioned with respect to one another in the absence of application of compressive and expensive forces to said guide, and such that relative movement between said guide and sheath is permitted by overcoming said frictional engagement through exertion of one of said compressive and expansive forces on said guide to adjust the effective diameter of said guide, and so that said slot is adapted to receive said catheter with said catheter being movable relative to said slot and said slot being readily enlarged at those portions adjacent to said catheter to facilitate catheter movement relative to said slot.

3. The catheter introducer device of claim 2 wherein said device includes means to maintain said reduced effective diameter of said guide during insertion of said device in a body.

4. A catheter placement unit having a trocar with a substantially cylindrical sheath, the improvement comprising:

a guide having a generally tubular configuration about its longitudinal axis;

said guide being made of a single curved piece of semirigid material having opposite longitudinally extending sides which are adjacent to one another and outer and inner surfaces which define a generally tubular wall therebetween having a preselected effective diameter;

said opposite longitudinally extending sides providing a slot extendable along the entire longitudinal length of said guide whereby the exertion of compressive forces on the outer surfaces of the guide causes rolling of the generally tubular wall to reduce the effective diameter of the guide and whereby the exertion of expansive forces on the inner surface of the guide causes unrolling of the generally tubular wall to enlarge the effective diameter of the guide, so that the effective diameter of said guide is such that frictional engagement of said guide with said sheath of said trocar exists when said guide and sheath are coaxially positioned with respect to one another in the absence of application of compressive and expansive forces to said guide. and such that relative movement between said guide and sheath is permitted by overcoming said frictional engagement through exertion of one of said compressive and expansive forces on said guide to adjust the effective diameter of said guide. and so that said slot is adapted to receive said catheter with said catheter being movable relative to said slot and said slot being readily enlarged at those portions adjacent to said catheter to facilitate catheter movement relative to said slot; and said catheter received in said guide and slot in said generally tubular wall including at least one cuff thereon.

* * * * *